United States Patent [19]
Ciamacco, Jr. et al.

[11] Patent Number: 5,772,642
[45] Date of Patent: Jun. 30, 1998

[54] CLOSED END CATHETER

[75] Inventors: Sam Ciamacco, Jr., San Diego; Mark A. Hoekwater, Carlsbad; Glen L. Lieber, Poway; Michael A. Baker, Rancho Santa Fe, all of Calif.

[73] Assignee: Medtronic, Inc., Minneapolis, Minn.

[21] Appl. No.: 801,987

[22] Filed: Feb. 19, 1997

[51] Int. Cl.$^6$ .................................................. A61M 25/00
[52] U.S. Cl. ........................... 604/280; 604/264; 604/49
[58] Field of Search ................................. 604/49, 53, 96, 604/102, 264, 280

[56] References Cited

U.S. PATENT DOCUMENTS

| | | | |
|---|---|---|---|
| 5,040,548 | 8/1991 | Yock | 128/898 |
| 5,061,273 | 10/1991 | Yock | 606/194 |
| 5,147,282 | 9/1992 | Kan | 600/1 |
| 5,199,939 | 4/1993 | Dake et al. | 600/3 |
| 5,267,958 | 12/1993 | Buchbinder et al. | 604/96 |
| 5,282,781 | 2/1994 | Liprie | 600/3 |
| 5,451,233 | 9/1995 | Yock | 606/194 |
| 5,501,227 | 3/1996 | Yock | 128/662.06 |
| 5,503,613 | 4/1996 | Weinberger | 600/3 |
| 5,540,659 | 7/1996 | Teirstein | 604/104 |

FOREIGN PATENT DOCUMENTS

| | | | |
|---|---|---|---|
| 857992 | 11/1961 | Germany | A61N 5/10 |
| 211066 | 1/1961 | United Kingdom . | |
| 9425106 | 11/1994 | WIPO | A61N 5/00 |
| 9610436 | 4/1996 | WIPO | A61M 29/00 |

OTHER PUBLICATIONS

Product Brochure; *Angioplasty USCI Accessories Dorros Infusion/Probing Catheter*, Jan. 1993.
Medtronic Interventional Vascular Brochure, *Buchbinder Transfer Catheter*, 1994.

*Primary Examiner*—Corrine M. McDermott
*Attorney, Agent, or Firm*—Dianne M. F. Plunkett; Harold R. Patton

[57] ABSTRACT

A method and apparatus for a closed end catheter system comprising a catheter body defining a tool lumen sized to receive an elongated tool. The distal end of the tool lumen has a plug therein. A guidewire lumen extends within the catheter body and is sized to receive a guidewire. The guidewire lumen extends along at least a portion of the length of the tool lumen such that the tool lumen and the guidewire lumen are in a biaxial relationship. The elongated tool has a distal tip and a working portion near the distal tip. Two marker bands are affixed to the catheter body and are separated from each other by a distance of not less than the length of the working portion of the tool. The elongated tool extends longitudially through the tool lumen such that when the distal end of the tool rests against the plug, the working portion of the tool is located between the first and second marker bands.

21 Claims, 7 Drawing Sheets

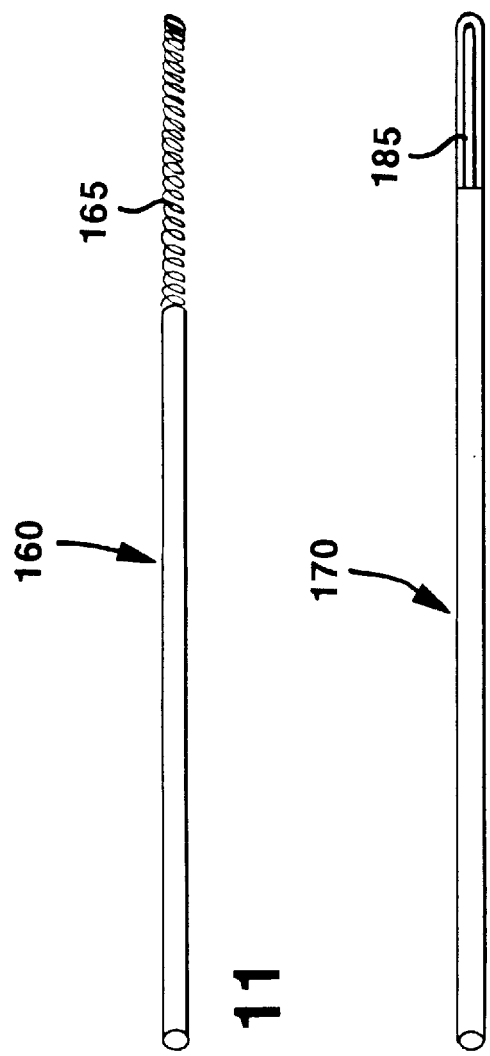

CLOSED END CATHETER

FIELD OF THE INVENTION

The present invention relates to a closed end catheter system for treatment or diagnosis in body lumens and more particularly to a single operator exchange design for crossing totally occluded lesions which delivers a variety of devices to a precise location.

BACKGROUND OF THE INVENTION

Percutaneous transluminal coronary angioplasty (PTCA) is used to increase the lumen diameter of a coronary artery partially or totally obstructed by a build-up of cholesterol fats or atherosclerotic plaque. Typically a first guidewire of about 0.038 inches in diameter is steered through the vascular system to the site of therapy. A guiding catheter, for example, can then be advanced over the first guidewire to a point just proximal of the stenosis. The first guidewire is then removed. A balloon catheter on a smaller 0.014 inch diameter second guidewire is advanced within the guiding catheter to a point just proximal of the stenosis. The second guidewire is advanced into the stenosis, followed by the balloon on the distal end of the catheter. The balloon is inflated causing the site of the stenosis to widen. The dilatation of the occlusion, however, can form flaps, fissures and dissections which threaten reclosure of the dilated vessel or even perforations in the vessel wall. A single operator exchange closed end catheter device may be needed for crossing totally occluded lesions or delivering devices that require a variety of lumen sizes.

Although the dimensions in the above example are suited to the coronary arteries, indications are not limited to coronary applications and any body lumen can be treated by percutaneous transluminal angioplasty (PTA), including the vas deferens, ducts of the gallbladder, prostate gland, trachea, bronchus and liver. The body lumens range in diameter from small coronary vessels of 3 mm or less to 28 mm in the aortic vessel. The applicant's closed end catheter system invention applies to acute and chronic closure or reclosure of any body lumen.

Single operator exchange (SOE) or "rapid exchange" devices were developed to respond to the disadvantage of the long (approximately 300 cm) "change" wire in the over-the-wire systems. Long wires are difficult to handle because such procedures require two operators who must be in communication during the procedure. This requires more time and risks contamination by dropping the guidewire from the sterile field. SOE devices have shorter guidewire lumens which enable the physician to anchor or hold the guidewire as the catheter is removed from the body with the exchange occurring over the shorter guidewire lumen.

A disadvantage of the prior art is not knowing the location of the operative therapy relative to the area of treatment. What is needed is a low cost, easy to manufacture design to deliver removable therapy devices have markers indicating the location of the therapy source without compromising the device profile and without damaging the surrounding tissues.

U.S. Pat. Nos. 5,040,548, 5,061,273, 5,451,233, 5,501, 227 to Yock disclose rapid exchange catheters.

U.S. Pat. No. 5,199,939 to Dake for a "Radioactive Catheter" discloses radioactive pellets which are held in place by short spacers between successive pellets.

U.S. Pat. No. 5,503,613 to Weinberger for an "Apparatus and Method to Reduce Restenosis after Arterial Intervention" discloses a radiation dose delivery wire with a radiation source encapsulated within its distal end and inserted into a blind lumen in a balloon catheter to deliver radiation to a target area of the patient's artery.

U.S. Pat. No. 5,540,659 to Teirstein for "Irradiation Catheter and Method of Use" discloses a radioactive source within the catheter, the catheter having a guidewire channel formed near its distal end. The catheter also has a closed end to retain the radioactive source within the catheter and a centering balloon or a set of centering wire loops to center the radioactive source radially within the blood vessel.

WO 96/10436 to Liprie for "Catheter for Maneuvering Radioactive Source Wire to Site of Treatment" discloses a guidewire that passes through the entire length of the catheter and exits through a constriction plug affixed to the end of the catheter. The constriction plug would prevent the radioactive source wire from remaining in the body after the catheter has been removed.

SUMMARY OF THE INVENTION

The present invention is accomplished by providing a method and apparatus for a closed end catheter system comprising a catheter body defining a tool lumen sized to receive an elongated tool. The distal end of the tool lumen has a plug therein. A guidewire lumen extends within the catheter body and is sized to receive a guidewire. The guidewire lumen extends along at least a portion of the length of the tool lumen such that the tool lumen and the guidewire lumen are in a biaxial relationship. The elongated tool has a distal tip and a working portion near the distal tip. Two marker bands are affixed to the catheter body and are separated from each other by a distance of not less than the length of the working portion of the tool. The elongated tool extends longitudinally through the tool lumen such that when the distal end of the tool rests against the plug, the working portion of the tool is located between the first and second marker bands.

BRIEF DESCRIPTION OF THE DRAWINGS

FIG. 11 is a plan view of a coiled radiation probe;

FIG. 12 is a plan view of an ultrasound device; and

DETAILED DESCRIPTION OF THE PREFERRED EMBODIMENTS

Applicant's single operator exchange closed end catheter system can be used for crossing totally occluded lesions or for delivering a variety of therapy devices. Closed end catheters 5 are advantageous because they allow catheter motion without exposing the artery to a sharp device thereby reducing the chance of perforations. Applicant's closed end catheter 5 can also have a thinner wall than conventional catheters as it can be structurally supported as required clinically by an appropriate tool such as a stylet, or other device.

Figure 7:
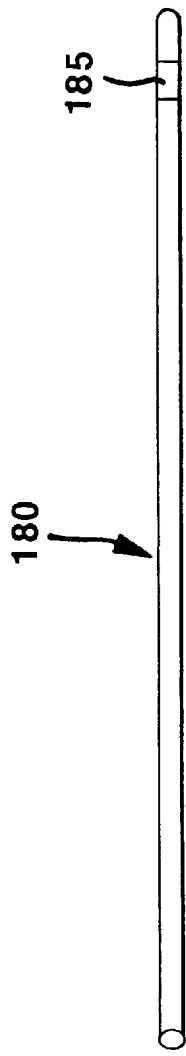
FIG. 7 is a plan view of a laser device.
Figure 13:
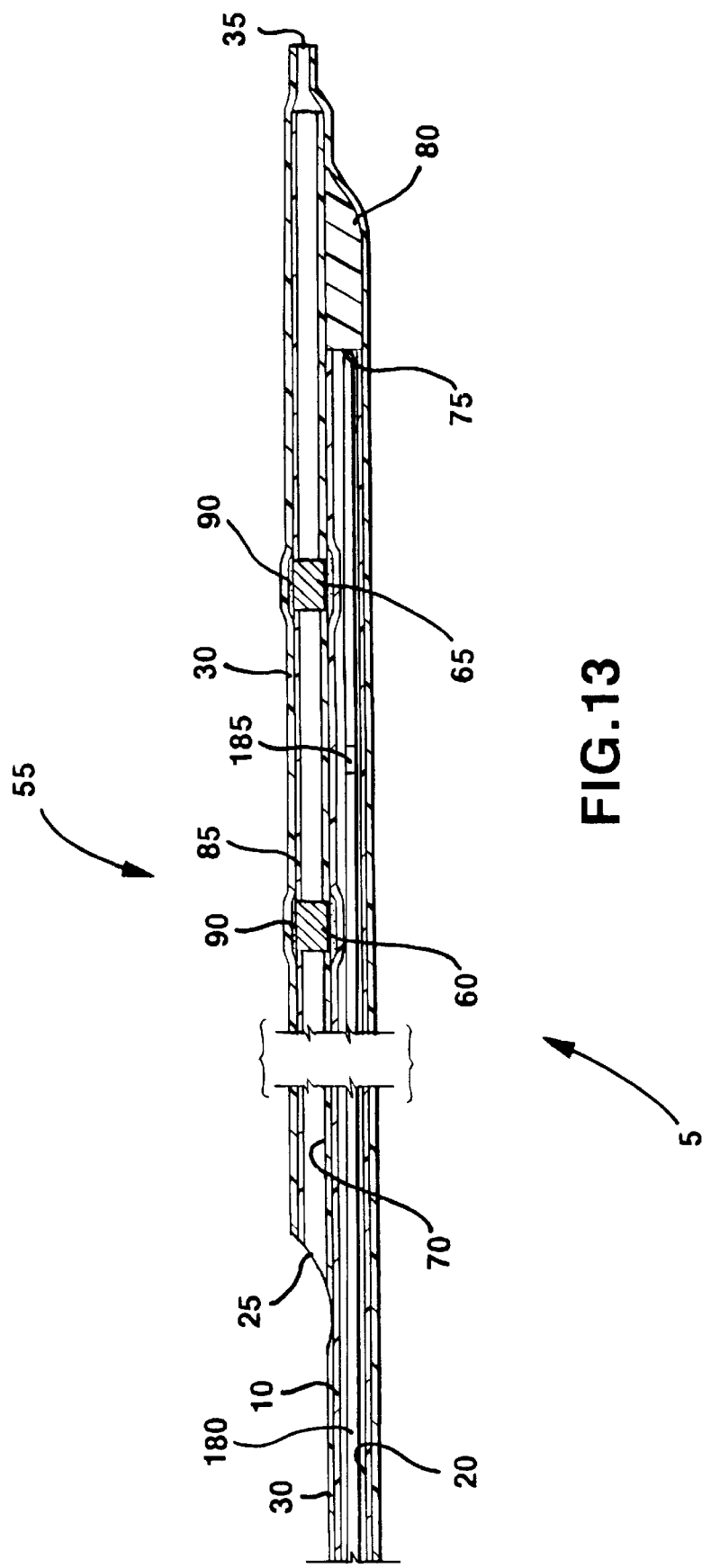
FIG. 13 is a longitudinal cross-section of the closed end catheter of FIG. 1B with the laser device of FIG. 7 inserted in the treatment lumen and with its laser module positioned centrally between the marker bands.

Applicant's closed end catheter 5 operates as follows. The distal end of the guidewire is located at the site of the therapy and the proximal end of the guidewire is placed into the guidewire lumen 70 via the guidewire exit port 35. Applicant's guidewire lumen 70 is biaxial with the treatment lumen 20. The guidewire lumen 70 and the treatment lumen 20 could be extruded or could be formed by separate tubes which could be bonded together. The closed end catheter 5 is then advanced over the guidewire to the treatment site. The treatment source tool having a working portion near its distal end is advanced into the treatment lumen 20. Marker bands 60 and 65 located on the exterior surface of the guidewire lumen 70 are used to position the treatment source tool in the distal section 55. When the treatment source tool's distal end pushes against the lumen stop 75, the working portion of the treatment source tool is in registration between the marker bands 60 and 65. The treatment source tool can then be slowly advanced between marker bands 60 and 65 as seen in FIG. 13 where the sample treatment source tool is the laser device 180 of FIG. 7 shown inserted in the treatment lumen 20 with its laser module 185 positioned centrally between the marker bands 60 and 65 and its distal end bearing on the lumen stop 75.

Figure 3:
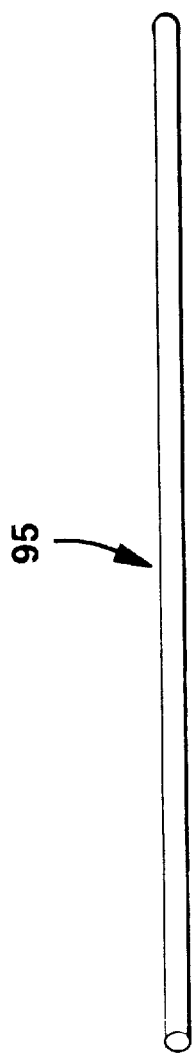
FIG. 3 is a plan view of a stylet.
Figure 4:
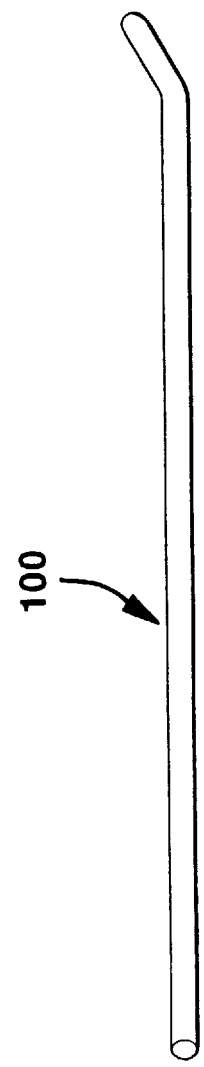
FIG. 4 is a plan view of a softly angled stylet.
Figure 5:
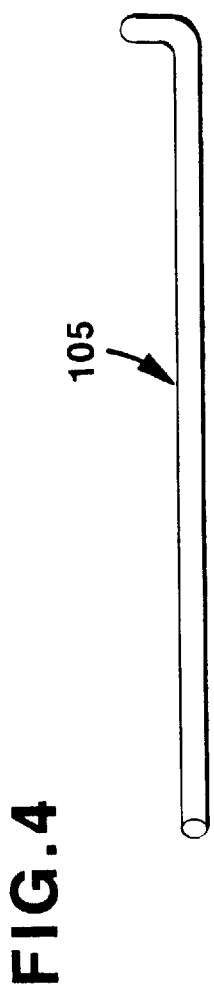
FIG. 5 is a plan view of a sharply angled stylet.

To cross a totally or a substantially occluded lesion applicant's invention can be used to deliver a substantial amount of force to the distal section 55 of the catheter 5. By having a plug 80 as close to the tip as possible, and by having the entire distal end secured by the shrink jacket tubing 30, a physician may drive the catheter 5 down a body lumen by pushing a tool such as a stylet 95 seen in FIG. 3 which is within the treatment lumen 20 rather than by pushing the catheter shaft. Applicant's lumen stop 75 with its blind/closed end is advantageous for crossing totally occluded lumens because of the ability to utilize multiple, potentially reusable stylets within a patient. The use of lumen stop 75 combined with shaped stylets such as the softly angled stylet 100 seen in FIG. 4, or the sharply angled stylet 105 seen in FIG. 5 and some type of movement to impart a unique probing action assists in crossing difficult lesions or in crossing occluded vessels or other body lumens. The distal end of the closed end catheter 5 will assume the shape of the distal end of the stylet 100, 105. Those skilled in the art would recognize that other non straight stylet tips could be used to therapeutic advantage.

Multiple stylets can be used to customize the catheter's 5 properties within a procedure. A very flexible stylet could be inserted into the treatment lumen 20 for optimal tracking to the lesion or clinical site and then a stiffer stylet could be inserted in order to provide optimal pushability and cross the lesion. Angled or shaped stylets 100, 105 are used to guide the catheter through very difficult anatomies. A stylet could be easily manipulated (moved in and out, rotated, vibrated, etc.) in order to impart a unique and specific motion to the tip of the catheter that could be used to better unocclude the vessel. Manually pushing an angle-tipped stylet 100, 105 in and out slightly can "peel" open (remove) the occlusion. An automated means to push the stylet or other device in and out could also be used to vary the frequency and amplitude of the motion and to tailor the motion to a specific lesion. Rotating an angle-tipped or spiral-tipped stylet could "peel" or "auger" or otherwise work open or cross the occlusion. Once the occlusion has been removed the guidewire can be advanced to perform the desired additional interventions such as PICA, stenting, etc. as appropriate. The stylet remains free of body fluids, results in reduced friction and furthermore permits the use of a tighter fit between the stylet and the catheter and therefore the closed end catheter 5 has a smaller profile.

In addition to stylets, applicant's closed end catheter 5 can be used to deliver devices that require a variety of lumen sizes such as x-ray devices 110, laser devices 180, magnetic probes 125, electrical probes 135, radiation probes 145, Inter Vascular Ultra Sound (IVUS) devices 170, atherectomy or other devices. The closed end lumen results from the lumen stop 75 at the plug 80. This closure prevents the inserted device from coming into direct contact with the patient's blood having the advantage of allowing the inserted device to be reused. Side holes could additionally be used to deliver drugs to localized zones.

Figure 6:
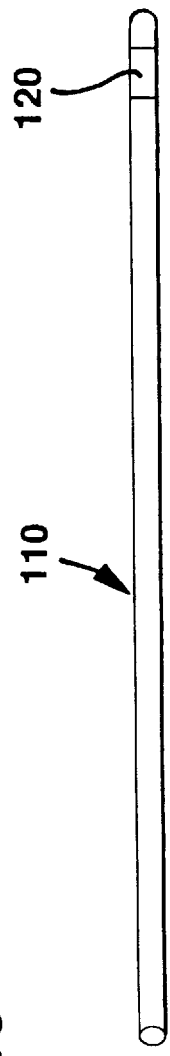
FIG. 6 is a plan view of an x-ray device.

An intravascular x-ray device 110 with an x-ray module 120 at the distal end as seen in FIG. 6, or a laser device 180 with a laser module 185 at the distal end as seen in FIG. 7 could be placed down the closed end catheter 5 treatment lumen 20, allowing diagnostic x-rays or laser therapy to be done from inside the vascular system. X-rays could also be used in intravascular radiation therapy. Applicant's closed end catheter 5 could shield x-rays from exiting except for at the specific treatment site. This could be achieved by material selection or jacketing with radiation shielding such as lead. The physician may also be able to "mirror" (reflect the rays down the length of the catheter, as for example with fiber optic cable) the treatment lumen 20 to provide shielding or ray transmission as desired (x-ray or other light). In the case of x-ray devices for diagnostic treatment, the source would be advanced down the treatment lumen 20 until it reached the lumen stop 75 where it would be in position to deliver the proper dosage. The marker bands 60, 65 indicate the location of the therapy source 120 or 185 without compromising the profile and without damaging the surrounding tissues. Therapy source 120 or 185 can be slowly moved between marker bands 60, 65.

Figure 8:
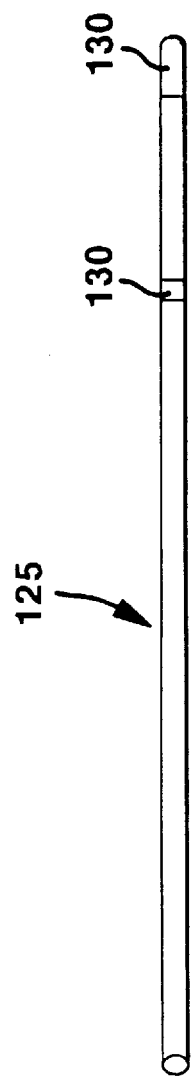
FIG. 8 is a plan view of magnetic probe.
Figure 9:
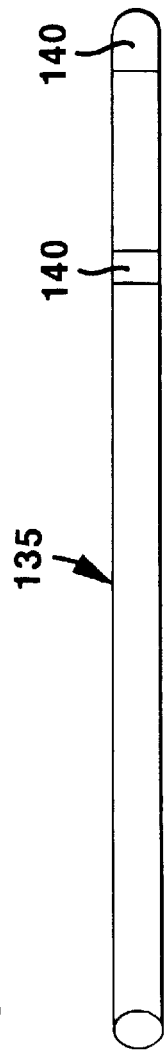
FIG. 9 is a plan view of an electrical probe.

Other devices, such as those for delivery of a magnetic probe 125 as seen in FIG. 8 or an electric probe 135 as seen in FIG. 9 to a portion of the vascular system could be administered using applicant's closed end catheter 5. This allows the use of a probe to put a magnetic module 130 or electrical module 140 across a lesion or other clinically relevant area to inhibit restenosis, scar tissue formation, or otherwise provide a clinical benefit. The closed end lumen catheter S prevents the inserted device from coming into direct contact with the patient's blood. This has the advantage of greater electrical safety. The marker bands 60, 65 indicate the location of the therapy source 130 or 140 without compromising the profile and without damaging the surrounding tissues. Therapy source 130 or 140 can be slowly moved between marker bands 60, 65.

Figure 10:
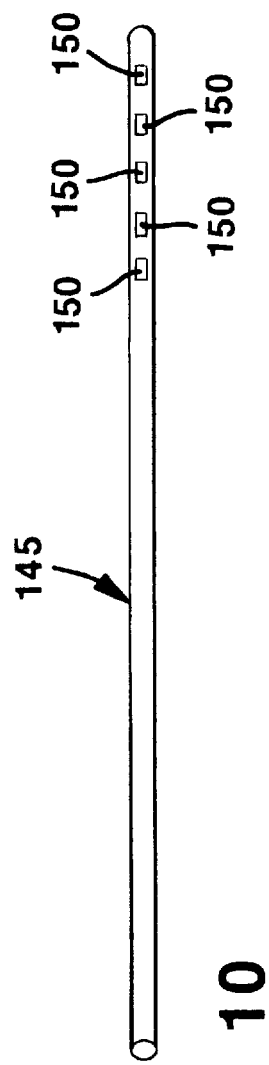
FIG. 10 is a plan view of a radiation probe.

The delivery of ionizing radiation such as highly penetrable radiation including gamma radiation, or low penetrating radiation such as beta radiation can impede the restenosis process. Applicant's closed end catheter 5 can be used with a radiation probe 145 as seen in FIG. 10 or a coiled radiation probe 160 as seen in FIG. 11. FIG. 10 shows radiation modules 150 and FIG. 11 shows radiation coil 165 although any conventional radiation probe of appropriate treatment lumen 20 size would be acceptable. The radioactive modules 150 or coil 165 can be made of any nuclide such as iridium. The markers 60, 65 indicate the location of the therapy source 150 or 165 without compromising the profile and without damaging the surrounding tissues. Therapy source 150 or 165 can be slowly moved between marker bands 60, 65.

Applicant's closed end catheter 5 can be used with an ultrasound device 170 as seen in FIG. 12. The closed end catheter 5 prevents the inserted device from coming into direct contact with the patient's blood as well as enabling the use of a separate, potentially less viscous solution to improve image resolution or reduce friction. An IVUS probe could be placed into the catheter to perform intravascular ultrasound during interventional procedures. It could also be used to determine centering considerations and dosage considerations when delivering intravascular radiation therapy. The markers 60, 65 indicate the location of the ultrasound module 175 therapy source without compromising the profile and without damaging the surrounding tissues. Therapy source 175 can be slowly moved between marker bands 60, 65.

Applicant's closed end catheter 5 can also be used with athrectomy devices. This assumes some cut-away portions of the sides at the distal end of the closed end catheter 5. With side portion(s) cut-away other tools which must come into contact with the arterial wall could be used as well.

The treatment tubing 10 which defines the treatment lumen 20 is made of High Density Polyethylene (HDPE). The guidewire tubing 85 defining the guidewire lumen 70 is made of High Density Polyethylene (HDPE). The jacket tubing 30 which encases the treatment tubing 10 and the guidewire tubing 85 is made of (HDPE). The plug 80 is made of Linear Low Density Polyethylene (LLDPE). The plug 80 could also be made of any radiopaque material which would be visible under fluoroscopy. The markers 60, 65 may be made of any radiopaque material. The profile of the catheter is reduced by affixing the markers 60, 65 to the exterior of the guidewire tubing 85.

The closed end catheter 5 for coronary use in radiation therapy is preferably approximately 66.93 inches (170 cm) long. For coronary uses in radiation therapy the catheter 5 must at least be longer than the standard 135 cm so that it can reach from the patient table to the table where the radioactive safe houses the radioactive source.

Figure 1A:
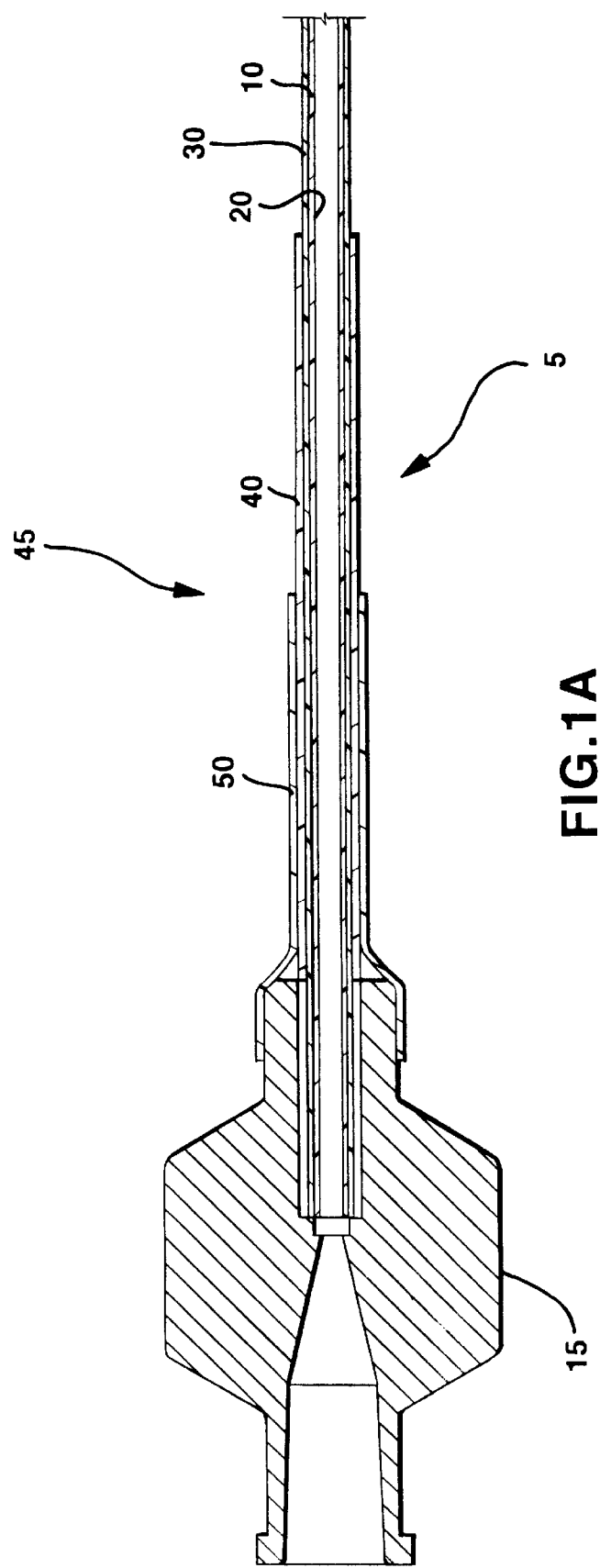
FIG. 1A is a longitudinal cross-section of the proximal end of the closed end catheter.
Figure 1B:
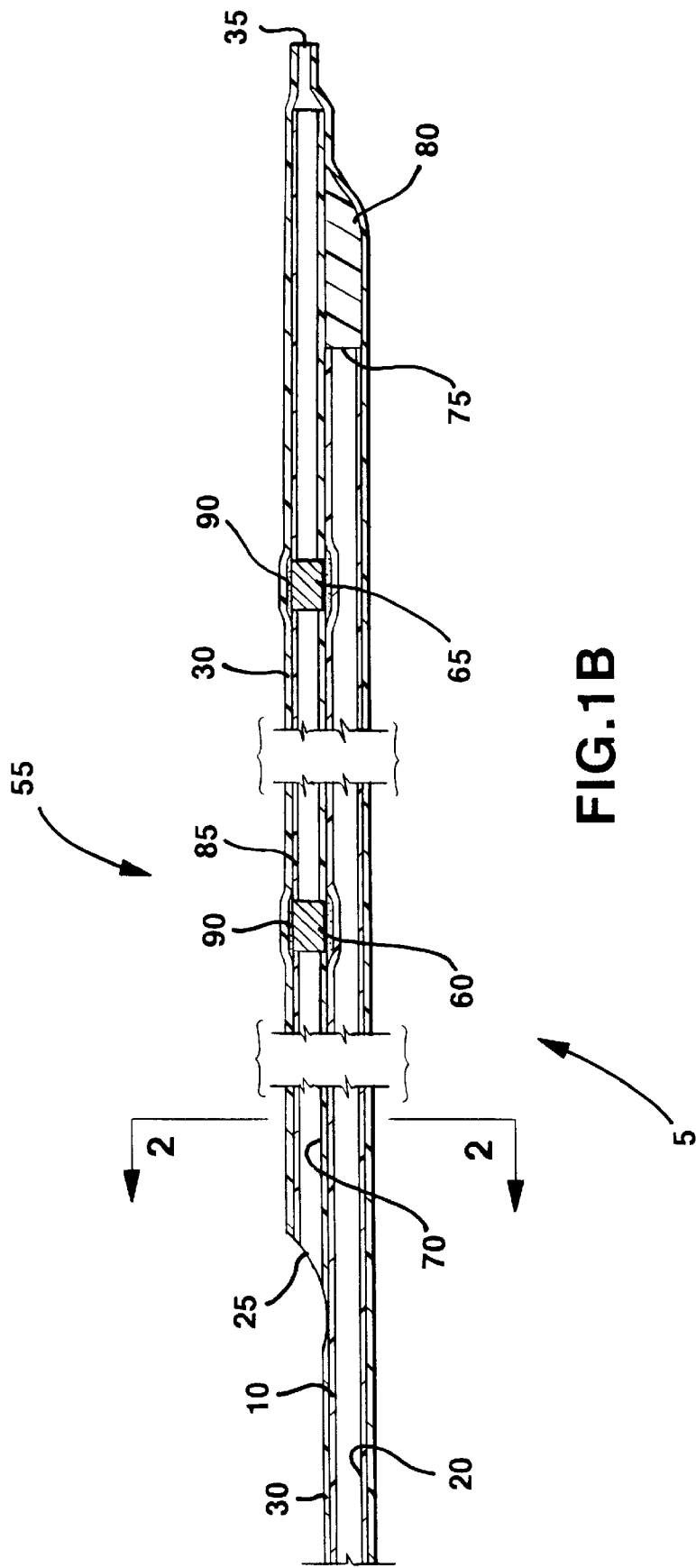
FIG. 1B is longitudinal cross-section of the distal end of the closed end catheter.
Figure 2:
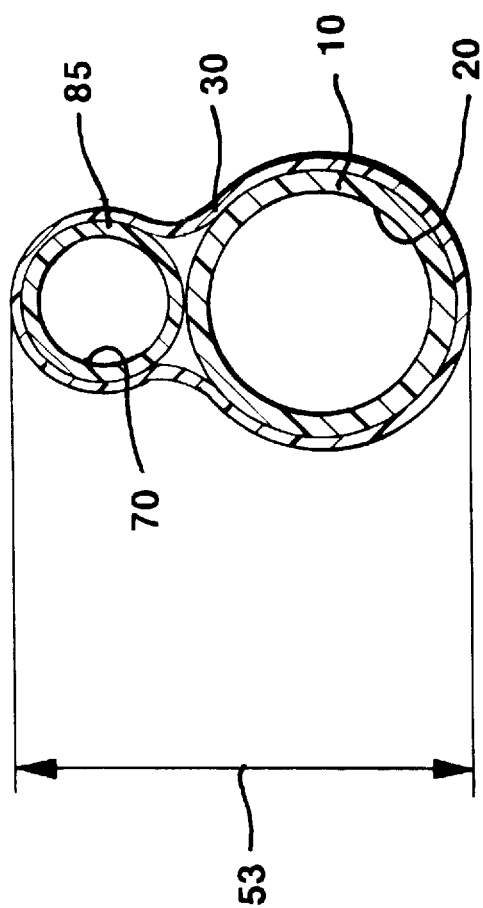
FIG. 2 is a cross-section taken along the lines 2—2 of FIG. 1B.

The treatment lumen 20 is sized to fit the desired device, having typically an inner diameter of 0.040 inches and an outer diameter of 0.050 inches for a 0.031 inch radiation probe 145 used in coronary applications. The jacket tubing 30 which encases the treatment tubing 10 and the guidewire tubing 85 has an outer diameter 53 of 0.070 inches (1.77 cm) at cross-section 2—2 seen in FIG. 2 given the above dimensions of the treatment tube 10 and guidewire tube 85.

For coronary applications using a standard 0.014 inch guidewire the guidewire tubing 85 length should preferably be from 1.0 cm to 25 cm with a most preferred length of 15 mm to 16 mm and a guidewire tube 85 outer diameter of 0.0205 inches with an inner diameter of 0.016 inches. the distal end of the jacket tubing 30 which extends beyond the guidewire tube 85 should be necked down such that the inner diameter is the same as that of the inner diameter of the guidewire tube 85 to prevent kinking. The outer diameter of the jacket tubing 30 which extends beyond the guidewire tube 85 is shaved to taper distally for increased flexibility. A 0.010 inch guidewire could also be used.

The proximal end of the first marker band 60 is approximately 5.886 in (149.50 cm) from the proximal end of the guidewire tubing 85. The marker bands 60, 65 are approximately 0.059 in (1.50 cm) long though any length which would be visible under fluoroscopy would be suitable. The distance between the distal end of the first marker band 60 and the proximal end of the second marker band 65 is approximately 1.142 in (29.0 cm). The length from the distal end of the second marker band 65 to the proximal end of the plug 80 is approximately 0.335 in (8.50 cm). These marker band dimensions and distances are suitable for coronary procedures using a radiation probe 145 although any distance between the marker bands and marker band dimensions suitable for the therapy being employed could be used.

Given the above dimensions, the length of the plug 80 is approximately 0.276 in (7.0 mm) with an outer diameter of 0.038 inches. The length from the distal end of the plug 80 to the distal end of the guidewire tubing 85 is 0.039 inches (1.0 mm). The length from the distal end of the guidewire tubing 85 to the distal end of the closed end catheter 5 is 2.0 mm. Thus the total distance from the tip of the plug 80 to the distal end of the closed end catheter 5 is 0.118 in (3.0 cm). It is important that the distance between the lumen stop 75 and the distal end of the closed end catheter not be greater than 2 cm and more preferably less than 1 cm. This is because with lengths greater than 1 cm beyond the distal end of the treatment device it will be difficult to get the treatment source to the distal vessels.

Assemble the closed end catheter 5 as follows. Cut the treatment tubing 10, jacket tubing 30, plug 80 and guidewire tubing 85 to length. Insert the marker bands 60, 65 on the exterior of the guidewire tubing 85. Loctite® 4014 (manufactured by Loctite Corp. in Hartford, Conn.) adhesive 90 is wicked under the marker bands 60, 65 to affix them to the exterior of the guidewire tubing 85. Those skilled in the art would recognize that the marker bands 60, 65 could be affixed by other methods and to other areas of the guidewire tube 85 as for example heat bonding to the inside of the guidewire tube 85. It is advantageous to affix the marker band to the guidewire tube 85 rather than to the treatment source tool as the marker bands 60, 65 could interfere with the treatment as for example affixing the marker bands 60, 65 to a radiation probe 145 would shield the radiation emitted.

Next, insert the plug 80 into the distal end of the treatment tubing 10 and heat bond it to affix it within. Heat shrink the jacket tubing 30 over the treatment lumen 20 and guidewire tubing 85. Heat shrink the area of the marker bands 60 and 65 until firmly held in place. Skive at an angle approximately 3 mm of the proximal end of the guidewire tubing 85 to create a guidewire entry port 25. This size skive will yield a suitably sized guidewire entry port 25 for a standard 0.014 inch guidewire and will slope in proportion to the above sized treatment tube 10. Attach the hub 15, the first strain relief 40 and second strain relief 50 to the proximal end of the proximal section 45. Those skilled in the art would recognize that many conventional hubs and strain reliefs would be suitable.

The preceding specific embodiments are illustrative of the practice of the invention. It is to be understood, however, that other expedients known to those skilled in the art or disclosed herein, may be employed without departing from the scope of the appended claims.

| No. | Component |
|---|---|
| 5 | Closed End Catheter |
| 10 | Treatment Tubing |

-continued

| No. | Component |
|---|---|
| 15 | Hub |
| 20 | Treatment Lumen |
| 25 | Guidewire Entry Port |
| 30 | Jacket Tubing |
| 35 | Guidewire Exit Port |
| 40 | First Strain Relief |
| 45 | Proximal Section |
| 50 | Second Strain Relief |
| 53 | Outer Diameter |
| 55 | Distal Section |
| 60 | First marker Band |
| 65 | Second Marker Band |
| 70 | Guidewire Lumen |
| 75 | Lumen Stop |
| 80 | Plug |
| 85 | Guidewire Tubing |
| 90 | Marker Band Adhesive |
| 95 | Stylet |
| 100 | Softly Angled Stylet |
| 105 | Sharply Angled Stylet |
| 110 | X-Ray Device |
| 120 | X-Ray Module |
| 125 | Magnetic Probe |
| 130 | Magnetic Module |
| 135 | Electrical Probe |
| 140 | Electrical Module |
| 145 | Radiation Probe |
| 150 | Radiation Modules |
| 160 | Coiled Radiation Probe |
| 165 | Radiation Coil |
| 170 | Ultrasound Device |
| 175 | Ultrasound Module |
| 180 | Laser Device |
| 185 | Laser Module |

What is claimed is:

1. A closed end catheter system comprising:
a catheter body having a proximal end and a distal end, the body defining a tool lumen sized to receive an elongated tool, the distal end of the tool lumen having a plug therein;
a guidewire lumen extending within the catheter body and sized to receive a guidewire, the guidewire lumen extending along at least a portion of the length of the tool lumen such that the tool lumen and guidewire lumen are in a biaxial relationship;
an elongated tool having a proximal end and a distal end, the elongated tool having a distal tip and a working portion near the distal tip;
a first marker band affixed to the catheter body;
a second marker band affixed to the catheter body and distal to the first marker band, the first and second marker bands being separated from each other by a distance not less than the length of the working portion of the tool; and
the elongated tool extending longitudinally through the tool lumen such that when the distal end of the tool rests against the plug, the working portion of the tool is located between the first and second marker bands.

2. A closed end catheter system comprising:
a treatment tube having a proximal end and a distal end, the treatment tube defining a treatment lumen sized to receive a cooperating treatment device, the distal end of the treatment tube being sealed with a plug;
a guidewire tube having a proximal end and a distal end, the guidewire tube defining a guidewire lumen sized to receive a guidewire, the guidewire tube being affixed to the treatment tube along at least a portion of the length of the treatment tube such that the treatment tube and guidewire tube are in a biaxial relationship;
a cooperating treatment device having a proximal end and a distal end, the cooperating treatment device having an operative treatment module affixed closer to the distal end of the cooperating treatment device than to the proximal end of the cooperating treatment device;
a first marker band affixed to an exterior surface of the guidewire tube;
a second marker band affixed to the exterior surface of the guidewire tube and distal to the first marker band, the first and second marker bands being separated from each other by a distance at least equal to the length of the operative module;
a jacket tube having the guidewire tube and the treatment tube extending longitudinally therethrough, the jacket tube being coaxial with the guidewire tube and the treatment tube; and
the cooperating treatment device extending longitudinally through the treatment lumen such that when the distal end of the cooperating treatment device rests against the plug, the operative treatment module is located between the first and second marker bands.

3. The closed end catheter system of claim 2 wherein the cooperating treatment device is a stylet having a proximal end and a distal end.

4. The closed end catheter system of claim 3 wherein the distal end of the stylet is not straight.

5. The closed end catheter system of claim 3 wherein the distal end of the stylet is at an angle.

6. The closed end catheter system of claim 2 wherein the cooperating treatment device is an x-ray device.

7. The closed end catheter system of claim 2 wherein the cooperating treatment device is a laser device.

8. The closed end catheter system of claim 2 wherein the cooperating treatment device is a magnetic probe.

9. The closed end catheter system of claim 2 wherein the cooperating treatment device is an electrical probe.

10. The closed end catheter system of claim 2 wherein the cooperating treatment device is a radiation device.

11. The closed end catheter system of claim 2 wherein the cooperating treatment device is an ultrasound device.

12. The closed end catheter system of claim 2 wherein the plug is radiopaque.

13. A method of treatment comprising:
providing a guidewire;
providing an elongated tool;
providing a catheter system comprising:
 a catheter body having a proximal end and a distal end, the body defining a tool lumen sized to slidingly receive the elongated tool, the distal end of the tool lumen having a plug therein,
 a guidewire lumen within the catheter body, the guidewire lumen sized to slidingly receive the guidewire, the guidewire lumen extending along at least a portion of the length of the tool lumen such that the tool lumen and the guidewire lumen are in a biaxial relationship,
 the elongated tool having a proximal end and a distal end, the elongated tool having a distal tip and a working portion near the distal tip,
 a first marker band affixed to the catheter body;
 a second marker band affixed to the catheter body and distal to the first marker band, the first and second marker bands being separated from each other by a distance of not less than the length of the working portion of the tool;
sliding the guidewire longitudinally through the guidewire lumen and locating a distal end of the guidewire at a treatment site within the body vasculature; and sliding the elongated tool longitudinally through the tool lumen such that when the a distal end of the tool rests against the plug, the working portion of the tool is located between the first and second marker bands.

14. A method of treatment comprising:

providing a guidewire;

providing a cooperating treatment device;

providing a closed end catheter comprising:
- a treatment tube having a proximal end and a distal end, the treatment tube defining a treatment lumen sized to slidingly receive the cooperating treatment device, the distal end of the treatment tube being sealed with a plug,
- a guidewire tube having a proximal end and a distal end, the guidewire tube defining a guidewire lumen sized to slidingly receive the guidewire, the guidewire tube being affixed to the treatment tube along at least a portion of the length of the treatment tube such that the treatment tube and guidewire tube are in a biaxial relationship,
- the cooperating treatment device having a proximal end and a distal end, the cooperating treatment device having an operative treatment module affixed closer to the distal end of the cooperating treatment device than to the proximal end of the cooperating treatment device,
- a first marker band affixed to an exterior surface of the guidewire tube;
- a second marker band affixed to the exterior surface of the guidewire tube and distal to the first marker band, the first and second marker bands being separated from each other by a distance at least equal to the length of the operative module,
- a jacket tube having the guidewire tube and the treatment tube extending longitudinally therethrough, the jacket tube being coaxial with the guidewire tube and the treatment tube;

sliding the guidewire longitudinally through the guidewire lumen and locating the distal end of the guidewire at a treatment site within the body vasculature; and sliding the cooperating treatment device longitudinally through the treatment lumen such that when a distal end of the cooperating treatment device rests against the plug, the operative treatment module is located between the first and second marker bands at the treatment site within the body.

15. The method of claim 14 further providing a stylet as the cooperating treatment device.

16. The method of claim 14 further providing an x-ray device as the cooperating treatment device.

17. The method of claim 14 further providing a laser device as the cooperating treatment device.

18. The method of claim 14 further providing a magnetic probe as the cooperating treatment device.

19. The method of claim 14 further providing an electrical probe as the cooperating treatment device.

20. The method of claim 14 further providing a radiation probe as the cooperating treatment device.

21. The method of claim 14 further providing an ultrasound device as the cooperating treatment device.

* * * * *